United States Patent [19]

Reich

[11] Patent Number: 6,070,281
[45] Date of Patent: Jun. 6, 2000

[54] PATIENT ORIENTATION TABLE

[75] Inventor: Gordon Reich, Forchheim, Germany

[73] Assignee: Siemens Aktiengesellschaft, Munich, Germany

[21] Appl. No.: 09/048,842

[22] Filed: Mar. 27, 1998

[30] Foreign Application Priority Data

Apr. 18, 1997 [DE] Germany ............... 197 16 381

[51] Int. Cl.[7] ................................. A61G 7/005
[52] U.S. Cl. ........................ 5/610; 5/611; 5/600
[58] Field of Search ............... 5/600, 601, 610, 5/611; 378/209; 108/7, 147

[56] References Cited

U.S. PATENT DOCUMENTS

| | | | |
|---|---|---|---|
| 1,573,571 | 2/1926 | Pohl ........................... | 5/601 X |
| 3,069,543 | 12/1962 | Savasky ....................... | 5/610 X |
| 3,797,050 | 3/1974 | Benoit et al. ................. | 5/610 |
| 3,805,080 | 4/1974 | Yager et al. .................. | 5/601 |
| 5,345,632 | 9/1994 | Langenaeken et al. ........ | 5/601 |
| 5,361,436 | 11/1994 | Hahn . | |
| 5,790,996 | 8/1998 | Narfstrom ..................... | 5/601 X |
| 5,864,901 | 2/1999 | Blumel ........................ | 5/610 |

*Primary Examiner*—Michael F. Trettel
*Attorney, Agent, or Firm*—Hill & Simpson

[57] ABSTRACT

A patient orientation table has a base, a carrier element in the form of a C-arm flexibly supported thereupon, a tabletop arranged on this carrier element which is variable in height by means of the C-arm and which is flexibly arranged at the C-arm, with a motorized drive for moving the C-arm, and a motorized drive for moving the tabletop. This latter drive is arranged at the C-arm in the region of the articulation point of the tabletop, and the drives are mutually coupled so that, given motion of the C-arm, the tabletop is readjusted while maintaining its momentary attitude.

15 Claims, 6 Drawing Sheets

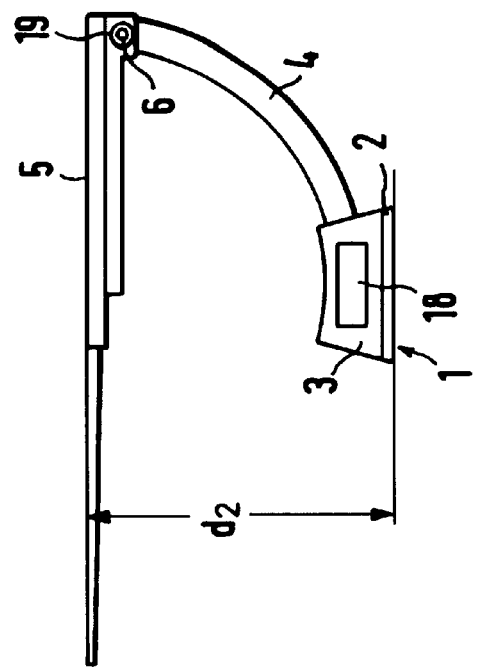
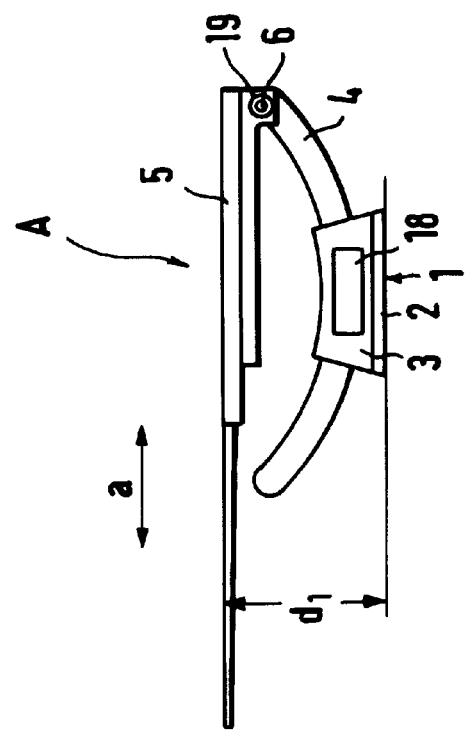

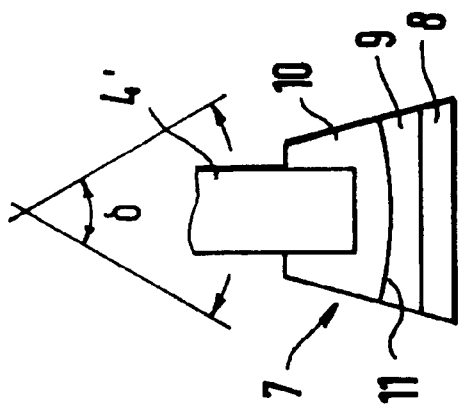
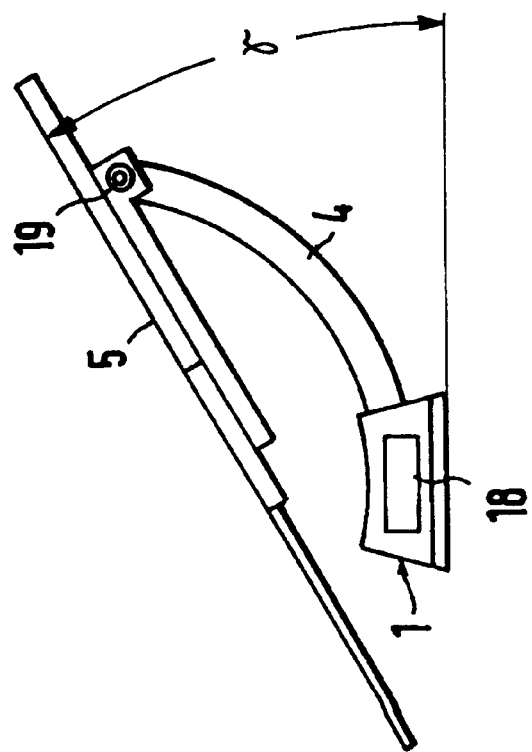
FIG 6
FIG 5

PATIENT ORIENTATION TABLE

BACKGROUND OF THE INVENTION

1. Field of the Invention

The present invention relates to a patient orientation table of the type having a base or pedestal, a carrier element in the form of a C-arm flexibly mounted thereupon, a tabletop flexibly arranged on this carrier element which is variable in height by means of the C-arm, a motorized drive means for moving the C-arm, and a motorized drive means for moving the tabletop, the latter drive means being arranged at the C-arm in the region of the articulation point of the tabletop.

2. Description of the Prior Art

Such patient orientation tables are used in connection with medical diagnostic and therapeutic devices, such as an X-ray device or the like, for example. They serve to receive the patient awaiting examination and are generally movable between a lowered position, in which the receiving of the patient is facilitated, and a raised position, in which the examination is then performed. This occurs by means of a carrier element which is flexibly supported at a base arranged at the floor side, this carrier element being vertically extensible in an upward fashion at this base. To this end, the carrier element is connected by a drive means in the form of a chain or the like, for example. In this context, one-piece carrier elements are known which generally permit a tabletop lift of 30 cm. In practice, this is frequently too little, since—proceeding from the necessary maximal height for treatment—the lowering is not sufficient in this case to enable a simple transfer of the patient from a sick-bed or the like. The minimal height is frequently still too high for older people as well. To counteract this, telescoping carrier elements exist which have two parts and which enable nearly double the lift, or around 60 cm. A disadvantage of these patient orientation tables is their complexity due to the telescoping carrier elements, this complexity resulting in considerably higher costs as well.

Furthermore, German OS 42 29 318 discloses a patient orientation table of the above type wherein the tabletop is swivelled about an axle which is fixed in place.

SUMMARY OF THE INVENTION

An object of the present invention to provide a patient orientation table of the type initially described having improved practical applicability and utility.

The above object is achieved in accordance with the invention in a patient orientation table of the type described initially wherein the drive means are mutually coupled so that, given motion of the C-arm, the tabletop is readjusted while its momentary attitude is maintained.

A motorized drive arrangement, particularly a toothed belt-toothed wheel drive, is provided for moving the C-arm at the base, this drive arrangement enabling a sufficiently exact and uniform motion of the C-arm. To enable motion of the tabletop which is flexibly arranged at the C-arm, a motorized drive arrangement is provided which is arranged at the C-arm in the region of the articulation at the tabletop, this drive arrangement producing the motion of the tabletop and achieving an exact and coordinated swivelling of the tabletop with respect to the C-arm. This drive arrangement can bring the tabletop into the desired position, which can be horizontal, but on the other hand can also be tilted with to the horizontal, depending on the respective desired examination method. The drive arrangement of the C-arm and of the tabletop are inventively mutually coupled so that, given motion of the C-arm, the tabletop is readjusted while maintaining its momentary attitude. This drive coupling is advantageous because, given motion from the lowered position to the raised position, the tabletop constantly remains in a horizontal attitude; that is, the patient lies quietly on the tabletop. Readjustment is of course equally possible for a tabletop which is swivelled out of the horizontal, e.g. if a CO2 exam is to be performed in the framework of which the tabletop stands essentially vertically. Due to the mobility of the C-arm, it is also possible to raise or lower the tabletop in its vertical height by swivelling the C-arm, wherein the vertical attitude is constantly maintained due to the coupling. For maximum utility, it is particularly advantageous for the tabletop to be flexibly arranged at the C-arm and to be able to be swivelled at an angle of at least 90°, in order to enable examinations to be performed in the horizontal or vertical patient attitude, for example. The tabletop can be further fixable in any angled attitude within the swivelling range.

To further improve the variability of the patient orientation table and thus its ability to be adjusted to the requirements presented in practice, besides the abovementioned swivelling options, in an embodiment of the invention the tabletop is variable in length, that is, the tabletop can be extended telescopically. In a further embodiment, the tabletop can also be arranged at the C-arm so that the former can be displaced longitudinally with reference to the latter; that is, the entire tabletop-mimic can be displaced with reference to the C-arm, which can be necessary if a correspondingly strong swivelling of the C-arm has been performed and one end of the tabletop is correspondingly lowered at the floor side. Transverse displace ability of the tabletop with reference to the C-arm, according to a further embodiment of the invention, is advantageous with respect to patient transfer,.

A C-arm is advantageously utilized as the carrier element in the patient orientation table, this C-arm being supported at the base in a displaceable fashion. Due to the curvature of the arm, the tabletop, which is arranged at one end of the C-arm, can be most easily modified in its height in a particularly advantageous fashion through the motion of the C-arm. Thus there is only one individual element, as is necessary in order for the construction of the patient orientation table to be simple, while simultaneously enabling a lift as required in practice.

In another embodiment of the invention, the C-arm is flexible with reference to the base along an essentially horizontal axle; that is, during the motion at the base the C-arm is displaced more or less horizontally. Alternatively, the C-arm can be inventively flexible along an essentially vertical axle with respect to the base; that is, the C-arm extends approximately from above to below at the base.

In accordance with the invention, it is preferable to arrange the tabletop at the C-arm at an end region of the tabletop, especially with an essentially horizontally flexible C-arm. Alternatively an essentially vertically flexible C-arm, the tabletop can be arranged at this C-arm in an essentially central region of the tabletop.

According to a further embodiment of the invention, the C-arm and with it the tabletop is supported at the base so that it can be swivelled about a vertical axle, preferably 90° thereabout, which enables it to receive the patient in the one tabletop position, for example, and subsequently to swivel into the actual examination position. Besides this horizontal swivelling ability, in a further embodiment of the invention the C-arm can be supported at the base so that it can be swivelled about an essentially horizontal axle, preferably 300 thereabout, which enables it to tilt the C-arm and the tabletop arranged thereat somewhat out of the horizontal, for example, which is advantageous for a simplified patient transfer.

DESCRIPTION OF THE DRAWINGS

FIGS. 1–5 show a first embodiment of an inventive patient orientation table, respectively in various attitudes FIG. 6 is a view of a base of an inventive patient orientation table in another embodiment.

DESCRIPTION OF THE PREFERRED EMBODIMENTS

Figure 4:
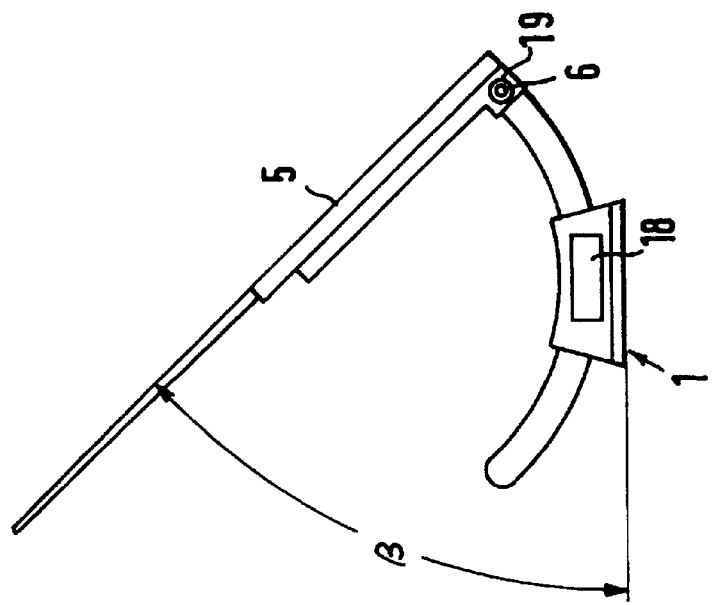

FIG. 1 shows a patient orientation table A according to a first inventive embodiment. The table A includes a base 1 arranged on the floor, having a stationary part 2 and a movable part 3 arranged at the stationary part 2, which part can be rotated about a vertical axle. A C-arm 4 is arranged at this movable part 3 so that this C-arm 4 can be displaced in a horizontal plane, as can be seem from the other figures. The C-arm 4 is dimensioned with a length corresponding to an arc of essentially 90°. At the right end of the C-arm 4 a tabletop 5 is connected in a swivelling fashion at articulation point 6, as likewise can be seen from the other figures. Drives 18 and 19 are provided not only to move the C-arm 4 along the movable part 3, but also to swivel the tabletop 5, these drives 18 and 19 being integrated in the movable part 3 (drive 18, in the form of a toothed belt-toothed wheel drive, for example), and in the region of the articulation point 6 (drive 19). These drives 18 and 19 are coupled to each other so that, given motion of the C-arm 4 out of the lowest position (see FIG. 1), in which patient transfer ensues, into the highest position (see FIG. 2), which corresponds to the examination position, the tabletop 5 remains constantly horizontal; that is, the tabletop 5 is constantly readjusted so as not to leave its horizontal attitude, for example, even with still more swivelling of the C-arm 4. As FIGS. 1 and 2 clearly show, a considerable lift is obtained by swivelling the C-arm 4 between the end positions depicted in these Figures. Thus, for example, the tabletop distance d1 equals ca. 60 cm. in the tabletop position depicted in FIG. 1; in contrast, the tabletop 5 is at a distance d2=120 cm from the ground in the position depicted in FIG. 2 (i.e. the total lift equals 60 cm).

Figure 3:
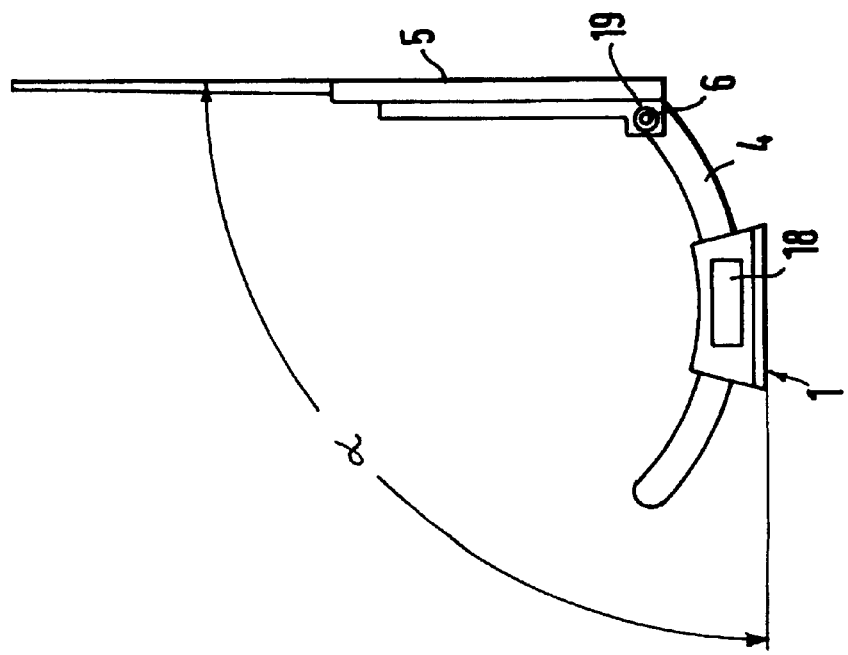
Figure 8:
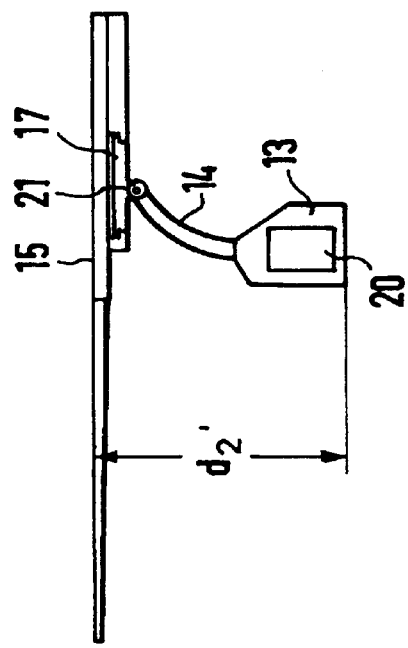
FIGS. 7–11 show an inventive patient orientation table according to another embodiment, respectively in various attitudes.
Figure 7:
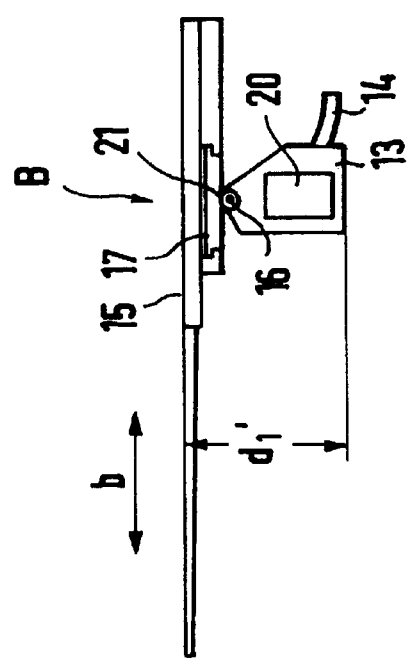

FIGS. 3, 4, and 5 show other attitudes of the inventive patient orientation table A. In the attitude depicted in FIG. 3, the tabletop 5 is swivelled into the vertical; i.e., $\alpha=90°$. Such an attitude is necessary for CO2 examinations, for example. The drive for the tabletop 5 allows the tabletop 5 to assume any inclination between the horizontal attitude depicted in FIG. 1 and the vertical attitude depicted in FIG. 3, as is clearly shown in FIG. 4, in which the angle $\beta$ equals 45°. Finally, an inclination of the tabletop 5 is also possible in the opposite direction, as depicted in FIG. 5. There the angle $\gamma$ equals 30°. To obtain this inclination, the C-arm 4 is swivelled out of the attitude depicted in FIG. 1, since it is not possible to incline the tabletop 5 without swivelling the C-arm 4, because the left free end of the C-arm 4 prevents this. As FIG. 5 further shows, the tabletop 5 is itself displaceable longitudinally with reference to the C-arm 4, this being necessary primarily with such an inclination, since otherwise the free end 6 if the tabletop 5 would be too close to the floor. The displaceability of the tabletop 5—which can also be telescopic in length,—also has advantages with respect to the positioning of the received patient.

FIG. 6 shows a further embodiment of a base 7. This base 7 likewise has a part 8 at the floor and a part 9 supported thereat which can be rotated about a vertical axle. In contrast to the previously described base 1, another part 10 is arranged at the part 9, the C-arm 4' being flexibly mounted at this part 10. This part 10 is supported so that it can be tilted along the guide 11 at part 9 at an angle $\delta$ i.e., it is possible in this inventive base 7 to tilt not only the C-arm but also the tabletop 5 carried thereby somewhat out of the vertical. This is advantageous particularly during patient transfer. The angle $\delta$ can equal 30°, for example.

Figure 10:
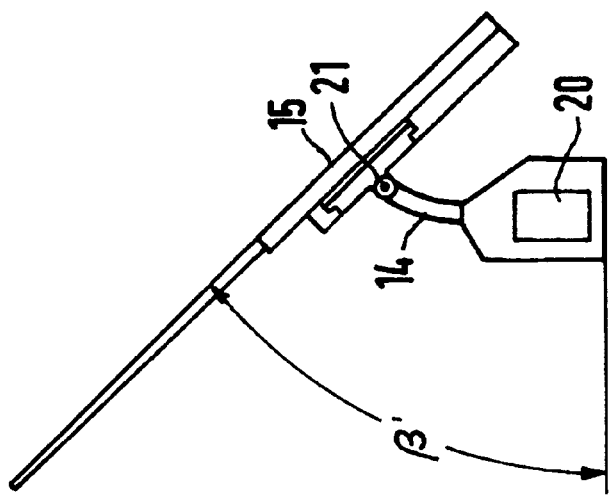
Figure 9:
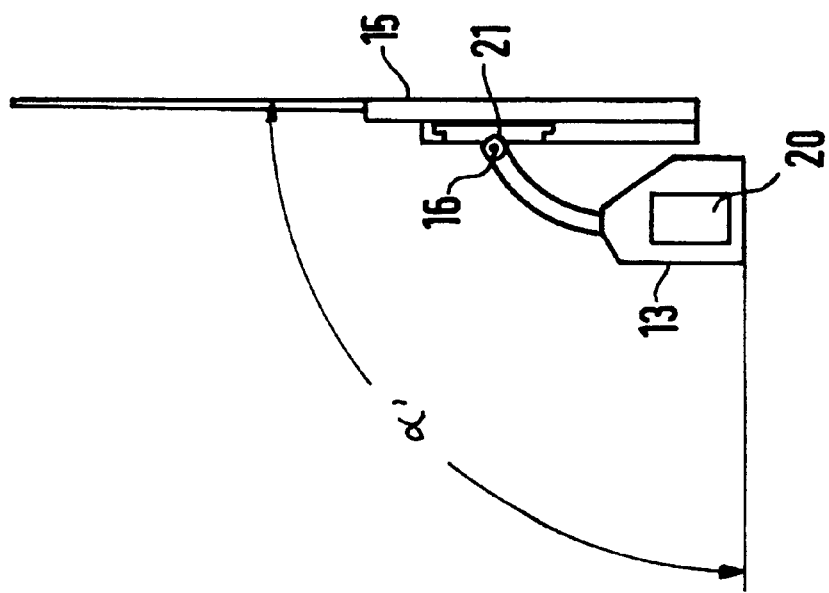
Figure 11:
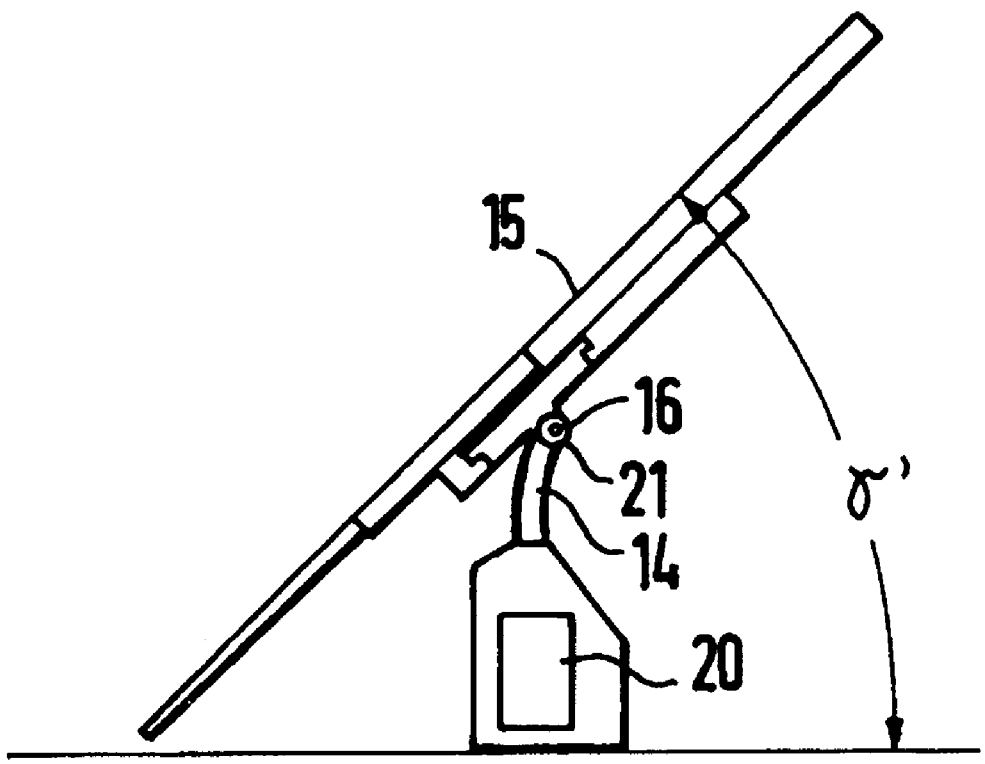

FIGS. 7–11 show another inventive embodiment of a patient orientation table B. This also has a base 13 at which a C-arm 14 is displaceably supported, wherein a drive 20, e.g. a toothed belt-toothed wheel drive can also be provided, as in the first embodiment. In the latter embodiment, however, the C-arm 14 is guided at the base 13 in an essentially vertically flexible fashion, as can be seen from FIGS. 8–11; that is, this C-arm 14 is insertable or extensible into this base 13 downwardly from above. A considerable lift can be realized there as well. Thus the distance d1' to the tabletop 15, arranged at one end of the C-arm 14 as well, equals 67.5 cm, for example. In the highest position, depicted in FIG. 8, the C-arm 14 is extended in its entirety out of the base 13, this C-arm 14 essentially corresponding to an arc of 90° therein as well. The tabletop distance d2' equals 115 cm.; that is, the lift realized therein equals 47.5 cm. In contrast to the embodiment depicted in FIGS. 1–5, the tabletop 15 is arranged at the C-arm 14 in a central region of the tabletop 15. As can be seen from FIGS. 9, 10 and 11, the most widely varying inclinations of the tabletop 15 can be set as well, this naturally being enabled also by means of a corresponding drive 21 engaging at C-arm 14 at the articulation point 16. The drives 20 and 21 are mutually coupled to enable a continuous readjustment of the tabletop 15, given motion of the C-arm 14. The tabletop 15 can be brought into a vertical attitude ($\alpha'=90°$) as well (cf. FIG. 9), any intermediary angle attitude can be assumed as well, as depicted in FIG. 10 ($\beta'=45°$). Due to the different guidance of the C-arm 4, a swivelling of the tabletop 15 is possible in the other direction as well—proceeding from the horizontal attitude (see FIGS. 7 and 11), since the free end of the C-arm 14 does not hinder swivelling until a swivel angle of several degrees is present. This means that in FIG. 7, the tabletop 15 can be easily positioned even without motion of the C-arm 14. FIG. 11 shows a swivelling in the other direction, wherein the angle $\gamma'$ equals 45° in this illustration. As can be seen from FIG. 11, the tabletop 15 can be displaced with respect to the C-arm 14 also, which is necessary for a swivelling in the direction depicted in FIG. 11, the corresponding angle of adjustment being otherwise unattainable, due to the mounting of the free end of the tabletop 15. The total angle range about which the tabletop 15 can swivel clearly equals more than 90°.

In the version of the patient orientation table depicted in FIGS. 7–11, the transverse displaceability of the tabletop 15 is realized with reference to the C-arm 14, besides the longitudinal displaceability of the tabletop 5. To this end, a guide part 17 is provided on which the tabletop 15 is received in a transversely displaceable fashion, this guide part 17 being itself connected at the C-arm 4 in an articulated fashion.

Although modifications and changes may be suggested by those skilled in the art, it is the intention of the inventor to embody within the patent warranted hereon all changes and modifications as reasonably and properly come within the scope of his contribution to the art.

I claim as my invention:

1. A patient orientation table comprising:
   a base;
   a carrier element comprising a C-arm movably supported on said base;
   a tabletop movably connected to said C-arm at an articulation point;
   first motorized drive means for slidably moving said C-arm relative to said base for varying a height of said tabletop;
   second motorized drive means for moving said tabletop relative to said C-arm, said second motorized drive means being disposed at said C-arm in a region of said articulation point; and
   said first and second motorized drive means being mutually coupled for, given movement of said C-arm, readjusting said tabletop while maintaining a momentary attitude of said tabletop.

2. A patient orientation table as claimed in claim 1 wherein said tabletop is disposed at said articulation point of said C-arm for movement by swiveling through an angle of at least 90°.

3. A patient orientation table as claimed in claim 2 wherein said tabletop is fixable at any angle attitude within a swivel range.

4. A patient orientation table as claimed in claim 2 further comprising means for varying a length of said tabletop.

5. A patient orientation table as claimed in claim 1 further comprising means for longitudinally displacing said tabletop relative to said C-arm.

6. A patient orientation table as claimed in claim 1 further comprising means for transversely displacing said tabletop relative to said C-arm.

7. A patient orientation table as claimed in claim 1 wherein said C-arm is movable with reference to said base along a substantially horizontal axle.

8. A patient orientation table as claimed in claim 1 wherein said C-arm is movable with reference to said base along a substantially vertical axle.

9. A patient orientation table as claimed in claim 1 wherein said tabletop has an end region, and wherein said tabletop is attached at said articulation point to said C-arm at said end region, and wherein said C-arm is substantially horizontally movable relative to said base.

10. A patient orientation table as claimed in claim 1 wherein said tabletop has an central region, and wherein said tabletop is attached at said articulation point to said C-arm at said central region, and wherein said C-arm is substantially vertically movable relative to said base.

11. A patient orientation table as claimed in claim 1 wherein said first motorized drive means comprises a toothed belt entrained around a driven toothed wheel.

12. A patient orientation table as claimed in claim 1 wherein said tabletop is supported at said base for allowing said tabletop to swivel around a vertical axle.

13. A patient orientation table as claimed in claim 12 wherein said tabletop is swivelable around said vertical axle through 90°.

14. A patient orientation table as claimed in claim 1 wherein said C-arm is supported at said base for swiveling around a horizontal axle.

15. A patient orientation table as claimed in claim 14 wherein said C-arm is swivelable around said horizontal axle through 30°.

* * * * *